United States Patent
Casey et al.

(10) Patent No.: US 11,207,136 B2
(45) Date of Patent: *Dec. 28, 2021

(54) SPINAL BALANCE ASSESSMENT

(71) Applicant: NuVasive, Inc., San Diego, CA (US)

(72) Inventors: Niall Casey, San Diego, CA (US); Jennifer Jassawalla, San Diego, CA (US); Eric Forman, San Diego, CA (US); Thomas Scholl, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 16/692,209

(22) Filed: Nov. 22, 2019

(65) Prior Publication Data

US 2020/0085503 A1    Mar. 19, 2020

Related U.S. Application Data

(63) Continuation of application No. 15/979,395, filed on May 14, 2018, now Pat. No. 10,507,061, which is a continuation of application No. 14/216,411, filed on Mar. 17, 2014, now Pat. No. 9,968,408.

(60) Provisional application No. 61/802,180, filed on Mar. 15, 2013.

(51) Int. Cl.
*A61B 34/10* (2016.01)
*G16H 50/50* (2018.01)

(52) U.S. Cl.
CPC ............ *A61B 34/10* (2016.02); *G16H 50/50* (2018.01); *A61B 2034/105* (2016.02)

(58) Field of Classification Search
CPC ... A61B 34/10; A61B 2034/105; G16H 50/50
USPC .......................................................... 703/6
See application file for complete search history.

(56) References Cited

U.S. PATENT DOCUMENTS

| | | | | |
|---|---|---|---|---|
| 4,773,402 A * | 9/1988 | Asher | ............. | A61B 17/7002 606/250 |
| 5,290,289 A * | 3/1994 | Sanders | ............. | A61B 17/7002 606/279 |
| 5,672,175 A * | 9/1997 | Martin | ............. | A61B 17/025 606/105 |
| 5,704,937 A * | 1/1998 | Martin | ............. | A61B 17/025 606/102 |
| 5,740,802 A * | 4/1998 | Nafis | ............. | G16H 50/50 600/407 |
| 5,765,561 A * | 6/1998 | Chen | ............. | G09B 23/28 348/77 |
| 5,880,976 A * | 3/1999 | DiGioia, III | ......... | A61B 17/155 703/7 |
| 6,226,548 B1 * | 5/2001 | Foley | ............. | A61B 17/7083 600/426 |

(Continued)

*Primary Examiner* — Justin C Mikowski

(57) ABSTRACT

The present application describes computer apparatus and software programs useful to the field of corrective spinal surgery. The apparatus and software implement and facilitate methods for assessing the degree of balance and alignment achieved through corrective measures applied to the spine prior to completing a surgical procedure. The apparatus and software facilitate pre-operative planning and virtual testing of the corrective measures to be applied. The apparatus and software further facilitate intra-operative reconciliation with the pre-operative plan prior to completing the surgery.

19 Claims, 6 Drawing Sheets

(56) References Cited

U.S. PATENT DOCUMENTS

| | | | | |
|---|---|---|---|---|
| 6,285,902 B1* | 9/2001 | Kienzle, III | | A61B 6/12 600/427 |
| 6,529,765 B1* | 3/2003 | Franck | | A61B 90/10 600/427 |
| 6,701,174 B1* | 3/2004 | Krause | | A61B 17/025 378/21 |
| 6,711,432 B1* | 3/2004 | Krause | | A61B 17/15 128/922 |
| 8,374,673 B2* | 2/2013 | Adcox | | A61B 17/1655 600/410 |
| 2003/0055502 A1* | 3/2003 | Lang | | G06F 30/00 623/16.11 |
| 2004/0068187 A1* | 4/2004 | Krause | | A61B 17/15 600/443 |
| 2004/0097952 A1* | 5/2004 | Sarin | | A61B 5/103 606/102 |
| 2004/0147927 A1* | 7/2004 | Tsougarakis | | A61F 2/30756 606/53 |
| 2004/0152972 A1* | 8/2004 | Hunter | | A61B 17/1703 600/424 |
| 2005/0245817 A1* | 11/2005 | Clayton | | A61B 5/06 600/424 |
| 2005/0288809 A1* | 12/2005 | Spaeth | | G05B 19/4099 700/98 |
| 2006/0212158 A1* | 9/2006 | Miller | | A61C 13/0004 700/163 |
| 2006/0235338 A1* | 10/2006 | Pacheco | | A61B 5/055 600/587 |
| 2007/0118055 A1* | 5/2007 | McCombs | | A61B 34/20 600/587 |
| 2008/0009945 A1* | 1/2008 | Pacheco | | A61F 2/4657 623/17.16 |
| 2008/0039717 A1* | 2/2008 | Frigg | | A61B 90/36 600/424 |
| 2008/0161680 A1* | 7/2008 | von Jako | | A61B 34/20 600/424 |
| 2008/0269596 A1* | 10/2008 | Revie | | A61F 2/4603 600/424 |
| 2008/0319275 A1* | 12/2008 | Chiu | | A61B 5/7289 600/300 |
| 2009/0018808 A1* | 1/2009 | Bronstein | | G16H 30/40 703/11 |
| 2009/0024164 A1* | 1/2009 | Neubardt | | A61B 5/1077 606/242 |
| 2009/0118714 A1* | 5/2009 | Teodorescu | | A61B 34/25 606/1 |
| 2009/0132050 A1* | 5/2009 | Holm | | A61F 2/30942 623/17.16 |
| 2009/0157083 A1* | 6/2009 | Park | | A61B 17/15 606/88 |
| 2009/0226068 A1* | 9/2009 | Fitz | | A61F 2/3603 382/131 |
| 2009/0276045 A1* | 11/2009 | Lang | | A61F 2/4657 623/14.12 |
| 2010/0030232 A1* | 2/2010 | Zehavi | | A61F 2/4611 606/130 |
| 2010/0100011 A1* | 4/2010 | Roche | | A61F 2/3859 600/587 |
| 2010/0183201 A1* | 7/2010 | Schwab | | G16H 30/20 382/128 |
| 2010/0191071 A1* | 7/2010 | Anderson | | G16H 20/00 600/301 |
| 2010/0191100 A1* | 7/2010 | Anderson | | G16H 20/40 600/424 |
| 2011/0066193 A1* | 3/2011 | Lang | | A61B 17/154 606/86 R |
| 2011/0071802 A1* | 3/2011 | Bojarski | | A61F 2/30942 703/1 |
| 2011/0121049 A1* | 5/2011 | Malinouskas | | A61B 90/98 227/175.1 |
| 2011/0305379 A1* | 12/2011 | Mahfouz | | A61B 8/4245 382/131 |
| 2011/0319745 A1* | 12/2011 | Frey | | A61B 34/10 600/407 |
| 2012/0010710 A1* | 1/2012 | Frigg | | A61B 34/20 623/16.11 |
| 2012/0116203 A1* | 5/2012 | Vancraen | | A61B 34/10 600/407 |
| 2012/0274631 A1* | 11/2012 | Friedland | | G16H 30/20 345/419 |
| 2013/0053854 A1* | 2/2013 | Schoenefeld | | A61B 90/92 606/87 |
| 2013/0072982 A1* | 3/2013 | Simonson | | A61B 17/7083 606/267 |
| 2013/0123850 A1* | 5/2013 | Schoenefeld | | A61B 17/7055 606/248 |
| 2013/0131486 A1* | 5/2013 | Copf | | A61F 2/30942 600/407 |
| 2013/0307955 A1* | 11/2013 | Deitz | | G06T 7/11 348/77 |
| 2013/0325069 A1* | 12/2013 | Pereiro de Lamo | | A61B 17/7062 606/263 |
| 2014/0081659 A1* | 3/2014 | Nawana | | G16H 50/50 705/3 |
| 2014/0188121 A1* | 7/2014 | Lavallee | | A61B 6/032 606/102 |

* cited by examiner

SPINAL BALANCE ASSESSMENT

CROSS REFERENCES TO RELATED APPLICATIONS

The present application is a continuation of U.S. patent application Ser. No. 15/979,395 (currently pending) filed on May 14, 2018, which is a continuation of U.S. patent application Ser. No. 14/216,411 (now U.S. Pat. No. 9,968,408) filed on Mar. 17, 2014, which claims priority to U.S. Provisional Application Ser. No. 61/802,180 filed on Mar. 15, 2013, the entire contents of which is hereby incorporated by reference into this disclosure as if set forth fully herein.

FIELD

The present invention relates to the field of corrective spinal surgery, including a system and associated methods for assessing the degree of balance and alignment achieved through corrective measures applied to the spine prior to completing the surgical procedure.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. Disruptions can be caused by any number factors including normal degeneration that comes with age, trauma, or various medical conditions. If a disruption to the spine becomes severe enough, damage to a nerve or part of the spinal cord may occur and can result in partial to total loss of bodily functions (e.g., walking, talking, breathing, etc.). Therefore, it is of great interest and concern to be able to treat and correct ailments of the spine.

When conservative efforts fail, treating spinal ailments very often includes a combination of spinal fusion and fixation. Generally, spinal fusion procedures involve removing some or all of an intervertebral disc, and inserting one or more intervertebral implants into the resulting disc space. Introducing the intervertebral implant serves to restore the height between adjacent vertebrae ("disc height") and maintain the height, and/or correct vertebral alignment issues, until bone growth across the disc space connects the adjacent vertebral bodies. During such procedures resection of ligaments and/or boney elements from the affected spinal area is common in order to access the disc space and/or decompress impinged nerve or spinal cord tissue. Though generally necessary to achieve the aims of the surgery, the resection of ligaments and/or boney tissue along the spine introduces instability (or, oftentimes, increased instability) to the spine.

Fixation systems are often surgically implanted during a fusion procedure to help stabilize the vertebrae to be fused until the fusion is complete or to address instabilities (either preexisting or created by the fusion or decompression procedure itself). Fixation constructs of various forms are well known in the art. Fixation systems usually use a combination of rods, plates, pedicle screws, and bone hooks to create a fixation construct across affected vertebrae. These fixations systems are designed to engage either the posterior elements (e.g. pedicle screw systems, spinous process plates) or anteriorly, the vertebral bodies (e.g. plates, anterior staple/rod systems). The configuration required for each procedure and patient varies due to the ailment being treated, the specific method of treatment (e.g. surgical approach, etc. . . . ) and the patient's specific anatomical characteristics. Like the fusion, the fixation system can be implanted across a single level or across multiple levels, and typically, the fixation system is positioned to span at least each level to be fused. In severe cases the fixation construct may stretch along the majority of the spine.

Despite the tremendous benefits gained by patients (e.g. a reduction or elimination of symptoms such as pain, poor posture, etc. . . . ) which can be credited to the fusion/fixation procedures, the procedures are not without disadvantages. For example, the loss of motion at one or more levels of the spine increases the loads placed on remaining untreated levels. These increased loads can hasten a breakdown at nearby untreated levels (commonly referred to as adjacent level disease), or, cause a hardware failure in which a portion of the spinal fixation construct breaks, generally leading to a failed fusion and instability. The importance of spinal balance as a determinant factor for positive surgical outcomes (those that avoid or limit the effects just described and result in a positive reduction of symptoms) is increasingly being recognized. Spinopelvic measurements have been identified as critical parameters to consider when evaluating overall balance. Several studies correlate worsening HRQL (Health Related Quality of Living) parameters with positive postoperative sagittal balance (defined as SVA>5 cm, PT>20°, PI≠LL±9°), where SVA=sagittal vertical axis, PT=pelvic tilt, and PI=pelvic incidence. Other relevant anatomical measurements include K=thoracic kyphosis, LL=lumbar lordosis, SA=sagittal alignment, CA=coronal alignment, T1-tilt. Tools to help the surgeon assess intraoperative changes in overall balance however are lacking. The tools and methods set forth herein are directed towards addressing these challenges.

DETAILED DESCRIPTION

The present application describes a balance assessment application that may be utilized by the surgeon before, during, and after surgery to ensure overall balance is achieved and maintained by the surgical procedure. The balance application includes a secure software package useable on portable computing devices (and preferably workstations as well) that manages patient data (images, relevant clinical information) and provides a platform for perioperative assessment and treatment. The application includes modules for pre-operative, intraoperative, and post-operative surgical measurement of anatomy, as well as manipulation and reconstruction of collected images.

Figure 1:
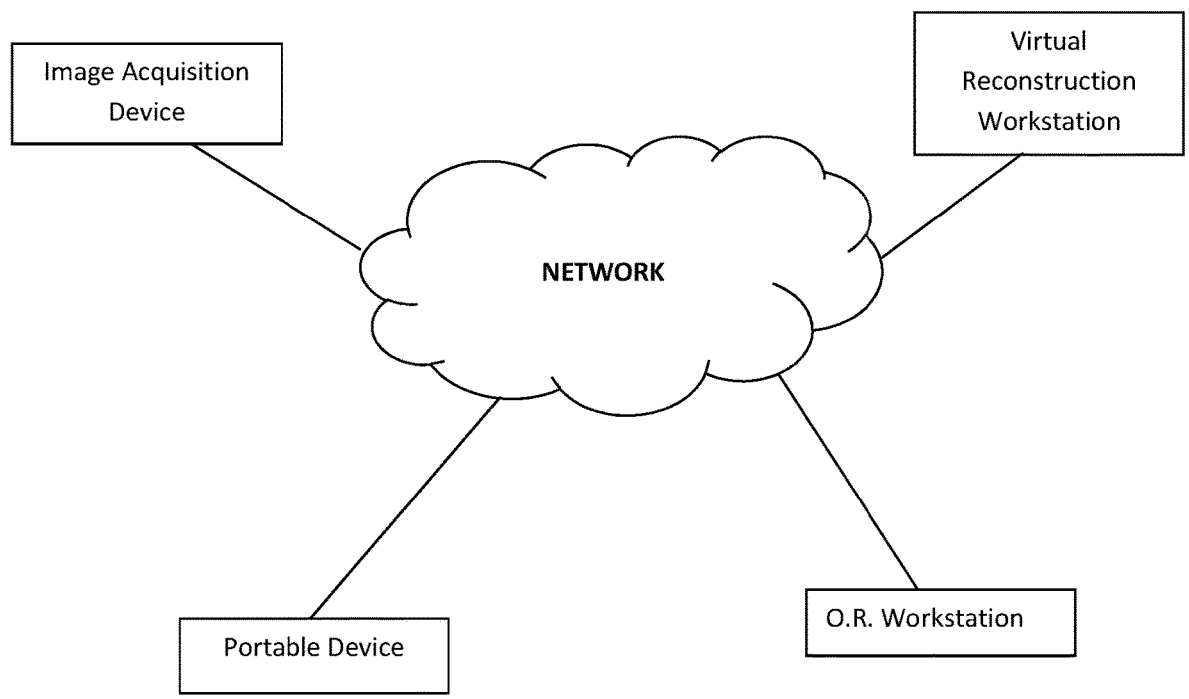
FIG. 1 is a flow chart depicting the network cloud structure utilized with the spinal balance assessment application described herein, according to one example embodiment.

With reference to FIG. 1, the balance assessment application utilizes a network structure (e.g. internet based cloud computing) that links a number of computer devices and diagnostic tools together over the internet. This structure enables secure data storage and transfer of diagnostic images for viewing on various computing devices (e.g. personal computers, tablets, or smart phones) and allows surgeons to access a patient's medical images at any time, with a variety of devices and on a variety of platforms to perform the clinical measurements for preoperative planning, intraoperative assessment and postoperative follow up. The surgeon can perform anatomical measurements directly on the mobile device, or on a separate workstation and then access the measurements later on the mobile device. The surgeon can also simulate the effects of surgical manipulations on postoperative alignment (e.g. simulate the effect of a 25° pedicle subtraction osteotomy) to maximize the surgeons ability to achieve overall balance. The balance assessment application may also utilize spatial mapping technology to evaluate intraoperative changes in alignment by tracking the location of anatomical landmarks. The spatial mapping technology may be similar to that described in U.S. patent application Ser. No. 13/815,643, filed Mar. 12, 2013 ("643 application"), which is incorporated herein by reference. It will be appreciated that the systems and software described in the Mar. 12, 2013 application may be used in conjunction with the spinal balance application described herein or may be integrated with the spinal balance application. It will also be appreciated that any of features, functions, tools, interfaces, etc. . . . described in the in the '643 application may be utilized in the spinal balance application to accomplish the same or related goals (e.g. spinal measurements, virtual manipulations, virtual reconstructions, etc. . . . ).

Figure 2:
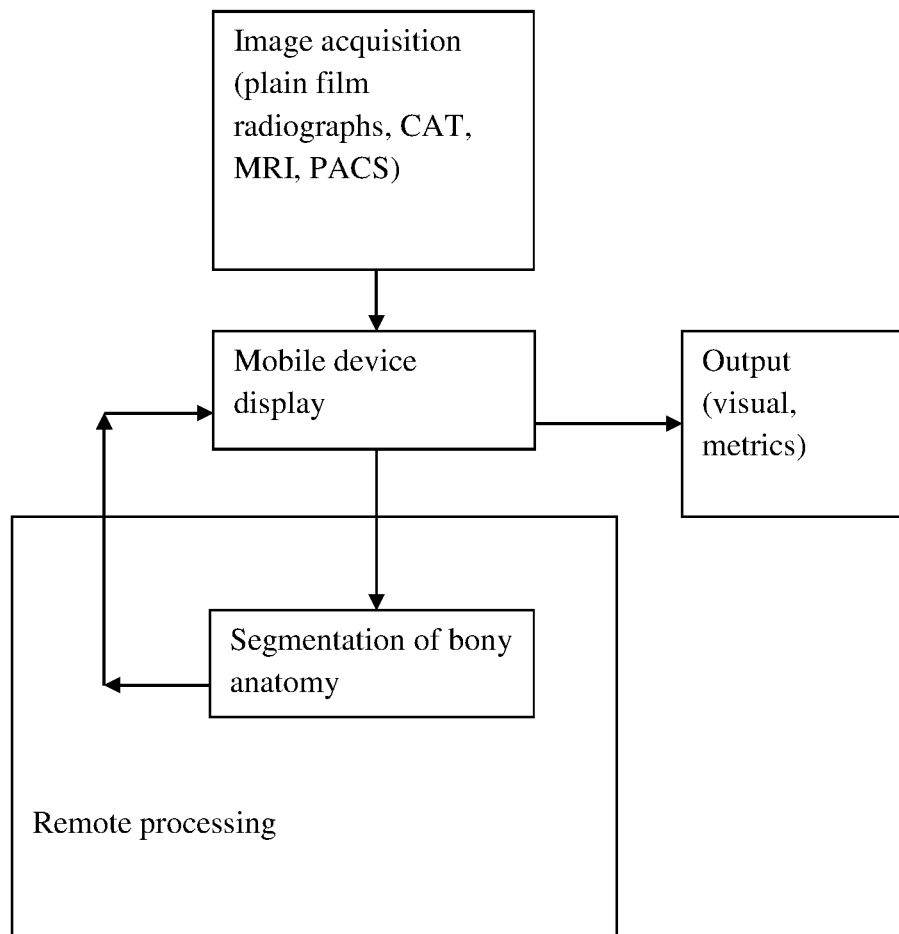
FIG. 2 is a flow chart depicting a preoperative module of the spinal balance assessment application described herein, according to one example embodiment.

The spinal balance application includes a preoperative module, a planning module, an intraoperative module, and postoperative module. With reference to FIG. 2, the preoperative module will now be described. The preoperative module begins with image acquisition. Pre-operative images (e.g. plain film radiographs, CAT, MM, PACS) are acquired from the hospital, doctors office, archive, etc . . . , and ported to the mobile device (e.g. laptop, tablet, smartphone) or other workstation. Optionally, the software package includes image recognition algorithms to detect bone in the images and automatically segments the bony anatomy such that the visual output only includes the bone structures. Metrics are performed on the bone structures to determine one or more of the anatomical measurements noted above. The metrics may be performed manually by the surgeon or assistant on a mobile device or workstation. By way of one example the software may include a GUI and the measurements may be calculated using the GUI. Still by way of example, the GUI may include the Virtual Protractor mode (or similar variation or modification) described in the '643 application. Alternatively, the metrics may be calculated automatically by algorithms in the software.

Figure 3:
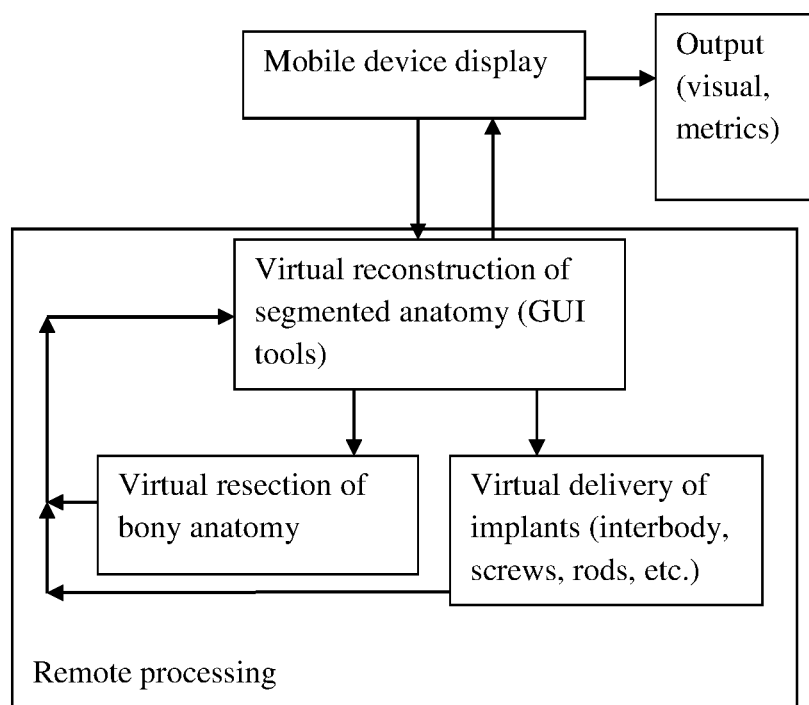
FIG. 3 is a flow chart depicting a surgical planning module of the spinal balance assessment application described herein, according to one example embodiment.

The surgical planning module is described now with reference to FIG. 3. Using the workstation (or mobile device if the processing power permits) a virtual reconstruction of the segmented anatomy may be performed. Using the GUI, the surgeon may resect boney anatomy, add implants (e.g. interbody devices, pedicle screws, rods, plates, etc. . . . ), and manipulate the position or alignment of anatomy. Metrics are performed to show the effects of the virtual surgery. Different degrees of manipulation, implant dimensions, and combinations thereof may be trialed until the desired correction and balance is achieved. The surgical plan (i.e. implant sizes, levels, resections, alignment manipulations, etc. . . . ) used to achieve the correction are saved for referral during the live surgery.

Figure 4:
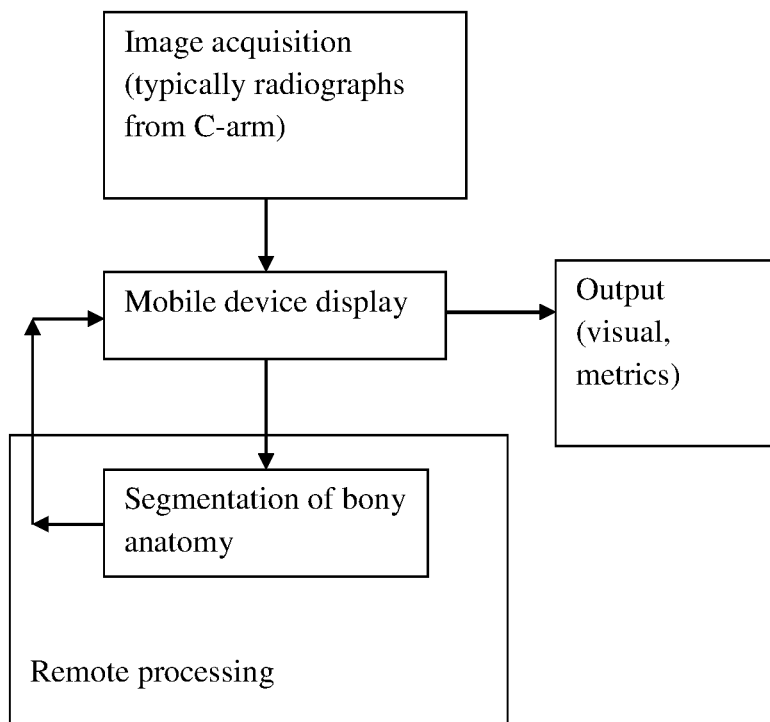
FIG. 4 is a flow chart depicting an intraoperative module of the spinal balance assessment application described herein, according to one example embodiment.

The intraoperative module is described with reference to FIG. 4. The intraoperative module begins with image porting of the surgical plan and preoperative imaging to the mobile device. Image acquisition (typically C-arm radiographs) occurs throughout the procedure as required and the images are ported to the mobile device or in O.R. workstation if available (it is noted that the processing system described in the '643 application may be utilized as the in O.R. workstation). The images are automatically segmented to provide easier visualization. The surgical plan can be viewed on the mobile device and followed during the live surgery to attempt to achieve the same correction and balance. Metrics are performed (again either manually as noted above, or automatically by the software) to reconcile the actual output with the virtual output. If the actual output does not comport with the virtual output, the surgeon may continue the operation and adjust one or more parameters of the reconstruction. This process may be repeated until the appropriate correction and balance is obtained.

Figure 5:
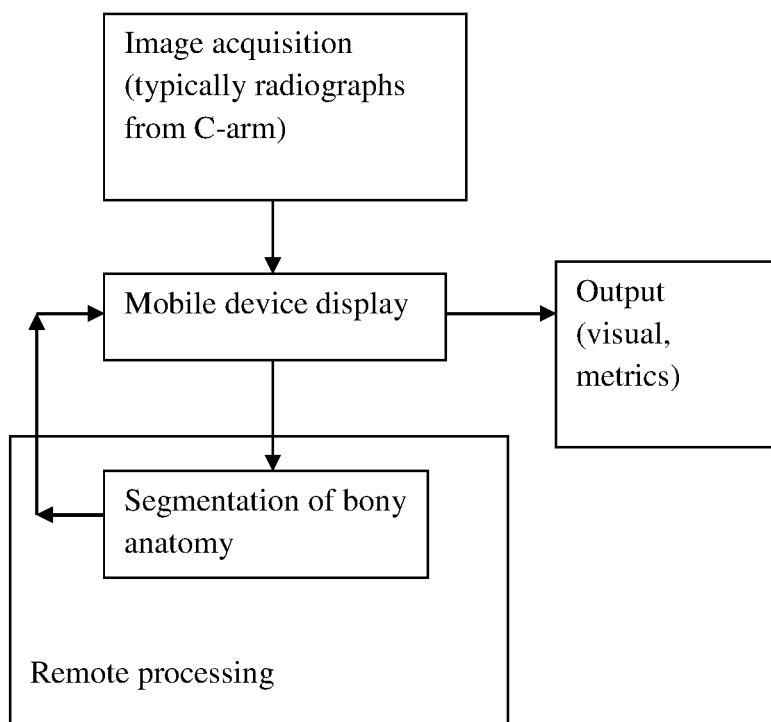
FIG. 5 is a flow chart depicting a postoperative module of the spinal balance assessment application described herein, according to one example embodiment.
Figure 6:
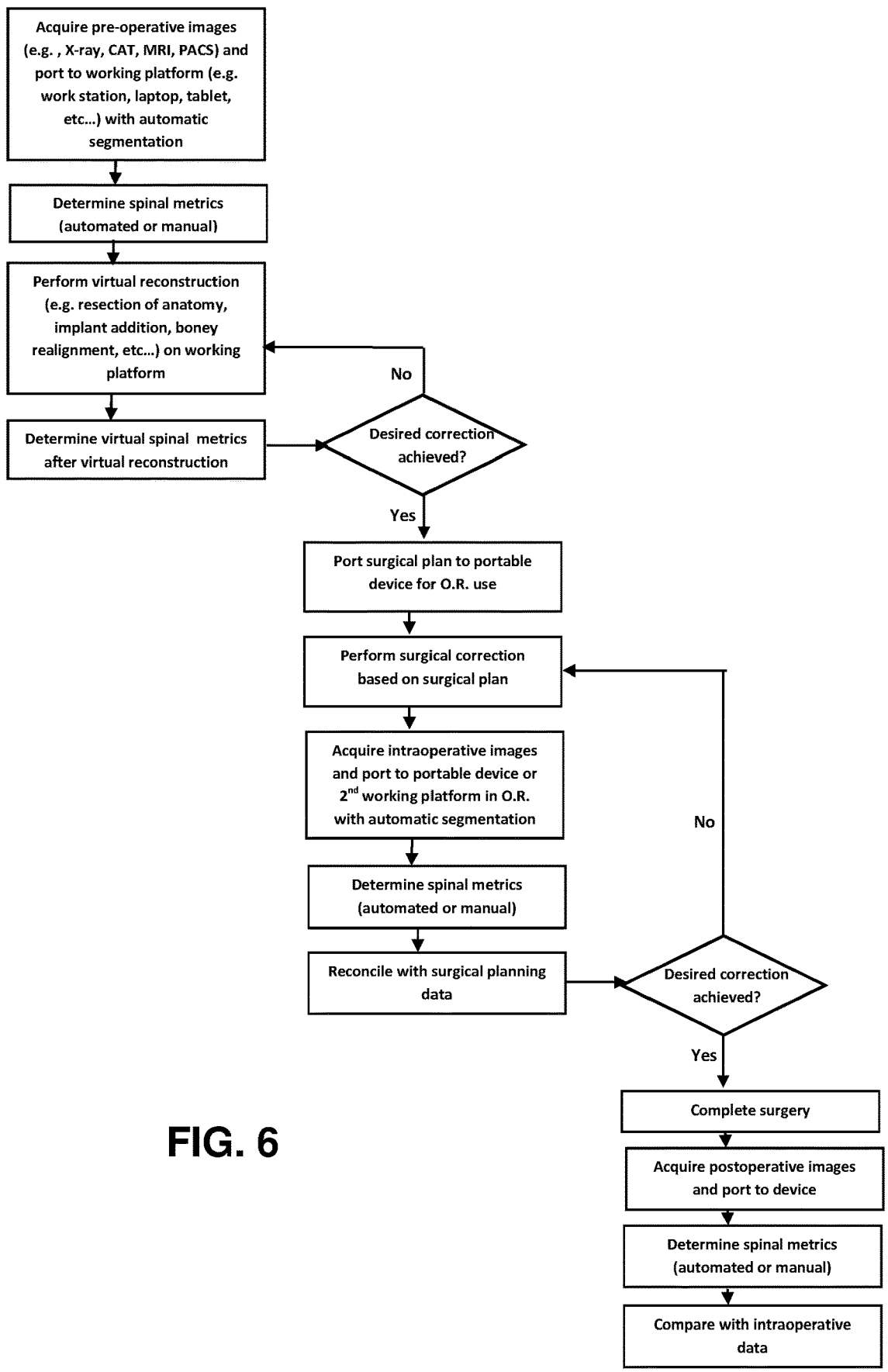
FIG. 6 is one example of a method for utilizing the spinal balance assessment application described herein for to ensure overall balance during a corrective spinal procedure.

The postoperative module is shown with reference to FIG. 5. The postoperative module is substantially similar to the preoperative module. However, in the postoperative module the postoperative metrics can be compared to the intraoperative metrics. This not only provides an ongoing assessment as to the overall balance of the spine, but it also provides data which can be collected and analyzed to aid in subsequent planning sessions. By way of example, FIG. 6 depicts one example method for using the spinal balance assessment application to ensure overall balance during a corrective spinal procedure.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

What is claimed is:

1. A method for assessing spinal balance during a surgical procedure executed on a surgical site on a spine of a patient, the method comprising:
   determining a preoperative numeric value of at least one spinal metric from a preoperative image of the surgical site based on a preoperative numeric relationship between two or more spinal landmarks that define the at least one spinal metric;
   determining a desired reconstruction numeric value of the at least one spinal metric based on a virtual reconstruction of the surgical site;
   performing a surgical correction on the surgical site based on the desired reconstruction numeric value;

determining an intraoperative numeric value of the at least one spinal metric from an intraoperative image of the surgical site based on an intraoperative numeric relationship between the two or more spinal landmarks;

reconciling the intraoperative numeric value of the at least one spinal metric from the intraoperative image with the desired reconstruction numeric value of the at least one spinal metric from the virtual reconstruction; and determining at least one spinal metric from a postoperative image and comparing the at least one spinal metric from the postoperative image with the at least one spinal metric from the intraoperative image.

2. The method of claim 1, wherein the virtual reconstruction includes at least one of anatomy resection, implant addition, and vertebral realignment.

3. The method of claim 2, wherein the anatomy resection is a pedicle subtraction osteotomy.

4. The method of claim 2, wherein the implant addition includes at least one of an interbody device, pedicle screw, rod, and plate.

5. The method of claim 1, further comprising:
segmenting the preoperative image to display only boney anatomy.

6. The method of claim 1, further comprising:
segmenting the intraoperative image to display only boney anatomy.

7. The method of claim 1, wherein determining the preoperative numeric value of at least one spinal metric from the preoperative image of the surgical site based on the preoperative numeric relationship between the two or more spinal landmarks that define the at least one spinal metric further comprises:
selecting the at least one spinal metric from the group comprising: sagittal vertical axis, pelvic tilt, pelvic incidence, thoracic kyphosis, lumbar lordosis, sagittal alignment, coronal alignment, or tilt.

8. The method of claim 7, wherein selecting the at least one spinal metric is based on a user input.

9. The method of claim 7, wherein selecting the at least one spinal metric is performed automatically.

10. The method of claim 1, further comprising:
determining at least one spinal metric from a postoperative image and comparing the at least one spinal metric from the postoperative image with the at least one spinal metric from the intraoperative image.

11. A method for assessing spinal balance during a surgical procedure executed on a surgical site on a spine of a patient, the method comprising:
determining a preoperative numeric value of at least one spinal metric from a preoperative image of the surgical site based on a preoperative numeric relationship between two or more spinal landmarks that define the at least one spinal metric;

simulating the effects of surgical manipulation by performing a virtual reconstruction of the surgical site;

determining a desired reconstruction numeric value of the at least one spinal metric from the virtual reconstruction;

performing a surgical correction on the surgical site based on the desired reconstruction numeric value;

determining an intraoperative numeric value of the at least one spinal metric from an intraoperative image of the surgical site based on an intraoperative numeric relationship between the two or more spinal landmarks;

reconciling the intraoperative numeric value of the at least one spinal metric from the intraoperative image with the desired reconstruction numeric value of the at least one spinal metric from the virtual reconstruction; and determining at least one spinal metric from a postoperative image and comparing the at least one spinal metric from the postoperative image with the at least one spinal metric from the intraoperative image.

12. The method of claim 11, wherein the virtual reconstruction includes at least one of anatomy resection, implant addition, and vertebral realignment.

13. The method of claim 12, wherein the anatomy resection is a pedicle subtraction osteotomy.

14. The method of claim 12, wherein the implant addition includes at least one of an interbody device, pedicle screw, rod, and plate.

15. The method of claim 11, further comprising:
segmenting the preoperative image to display only boney anatomy.

16. The method of claim 11, further comprising:
segmenting the intraoperative image to display only boney anatomy.

17. The method of claim 11, wherein determining the preoperative numeric value of at least one spinal metric from the preoperative image of the surgical site based on the preoperative numeric relationship between the two or more spinal landmarks that define the at least one spinal metric further comprises:
selecting the at least one spinal metric from the group comprising: sagittal vertical axis, pelvic tilt, pelvic incidence, thoracic kyphosis, lumbar lordosis, sagittal alignment, coronal alignment, or tilt.

18. The method of claim 17, wherein selecting the at least one spinal metric is based on a user input.

19. The method of claim 17, wherein selecting the at least one spinal metric is performed automatically.

* * * * *